United States Patent [19]
Sherwin

[11] Patent Number: 4,678,865
[45] Date of Patent: Jul. 7, 1987

[54] LOW NOISE ELECTROENCEPHALOGRAPHIC PROBE WIRING SYSTEM

[75] Inventor: Gary W. Sherwin, South Huntingdon Township, Westmoreland County, Pa.

[73] Assignee: Westinghouse Electric Corp., Pittsburgh, Pa.

[21] Appl. No.: 727,060

[22] Filed: Apr. 25, 1985

[51] Int. Cl.$^4$ .................................... H01B 11/18
[52] U.S. Cl. .................... 174/36; 174/71 R; 174/74 R; 174/103
[58] Field of Search .............. 174/36, 71 R, 74 R, 174/103, 106 R; 333/243; 128/639–644, 731

[56] References Cited

U.S. PATENT DOCUMENTS

| | | | |
|---|---|---|---|
| 2,234,068 | 3/1941 | Wiseman | 174/103 |
| 2,409,033 | 10/1946 | Garceau | 128/644 X |
| 2,622,152 | 12/1952 | Rosch | 174/36 |
| 3,107,152 | 10/1963 | Ford et al. | 174/36 |
| 3,433,687 | 3/1969 | Price | 174/36 |
| 3,669,095 | 6/1972 | Kobayashi et al. | 174/74 R |
| 3,692,925 | 9/1972 | Kindij | 174/36 X |
| 4,059,724 | 11/1977 | Ide | 174/36 |
| 4,374,299 | 2/1983 | Kincaid | 174/36 |
| 4,404,424 | 9/1983 | King et al. | 174/36 X |
| 4,599,483 | 7/1986 | Kuhn et al. | 174/103 X |

FOREIGN PATENT DOCUMENTS 3337432 4/1985 Fed. Rep. of Germany ........ 174/36

Primary Examiner—Morris H. Nimmo
Attorney, Agent, or Firm—Daniel C. Abeles

[57] ABSTRACT

A low noise EEG probe wiring system that substantially eliminates noise picked up by the loop enclosed by the cables of the wiring system, electrostatic and magnetic noise, and noise due to triboelectric effects. The low noise EEG probe wiring system comprises a pair of coaxial cables each including a central connector, a graphite coated insulating layer positioned around the central conductor, a first braid shield positioned around the graphite coated insulating layer and along the length of the coaxial cable, and a first insulator layer positioned around the first braid shield and along the length of the coaxial cables. The coaxial cables are positioned in contact with each other along a first portion of the length of the cables; a second braid shield positioned around the pair of coaxial cables and along the first portion of the length of cables and around each one of the cables along the remaining portion of the length of the cables and being connected to the first braid shield; and a second insulator layer positioned around the second braid shield.

2 Claims, 4 Drawing Figures

LOW NOISE ELECTROENCEPHALOGRAPHIC PROBE WIRING SYSTEM

CROSS REFERENCE TO RELATED APPLICATIONS

The present invention is related to the following co-pending and concurrently filed U.S. patent applications assigned to Westinghouse Electric Corporation: Electroencephalographic Cap by Sherwin having U.S. Ser. No. 727,031 filed 4/25/85; Evoked Potential Autorefractometry System by Bernard, Roth, Mohan, Sherwin and Zomp having U.S. Ser. No. 727,032 filed 4/25/85; and Electroencephalographic Amplifer by Zomp and Sherwin having U.S. Ser. No. 727,056 filed 4/25/85.

BACKGROUND OF THE INVENTION

1. Field of the Invention

This invention relates to electroencephalographic (EEG) probe lead wiring, and more particularly to a lead wire for an EEG probe which minimizes the noise introduced into an EEG measuring system due to the wiring between an EEG probe and an amplifier of an evoked potential autorefractometry system.

2. Description of the Related Art

In EEG systems, signals detected by the EEG probes are typically amplified by one million. Amplifiers for this purpose normally include very expensive low pass filters to filter out the noise picked up by the EEG probe and wiring between the probe and the amplifier. FIG. 1 illustrates a conventional EEG measurement system. In FIG. 1, noise due to lead wires 10 and 15, respectively connected between the EEG probes 20 and 25 and the amplifier 30, comprises four elements: (1) loop noise due to the area 35 enclosed by the lead wires 10 and 15, (2) electrostatic noise picked up by the lead wires 10 and 15, (3) microphonic noise due to variable capacitance between the lead wires, bending of and vibrations of the lead wires, and (4) triboelectric noise due to static charge pickup as a result of mechanical rubbing of a conductor over an insulator when the wire is bent.

Because the amplifier 40 amplifies the differential signals detected by the EEG probes 20 and 25, respectively, by approximately one million, and because the amplitude of the signals detected by the EEG probes 20 and 25 is similar to that of the noise due to the lead wires 10 and 15, it is essential that the lead wires introduce little if any noise into the measurement system. Previous attempts at minimizing the noise introduced into the measurement system by the lead wires between EEG probes and an amplifier included using an expensive low pass filter 45 to attenuate the noise due to the lead wires. This approach is only effective for noise having a frequency greater than the frequency of the signal sought to be detected. For example in EEG systems, use of such an expensive low pass filter can be effectively used to attenuate noise having a frequency greater than, 10 Hz.

Another prior attempt at minimizing the noise due to EEG lead wires included using microphone cables for each of the lead wires 10 and 15. Typical systems using such cables, however, terminate the microphone cable shielding at, for example, the metal frame of a bed upon which the subject to be analyzed was resting. As a result, about 3 to 4 feet of unshielded lead wiring normally is used between the position at which the microphone shielding is attached to the metal frame and the EEG probes. In addition to being susceptible to electrostatic noise, this approach does not address either the noise due to the loop area 35 or the triboelectric effect noise.

Twisting the lead wires 10 and 15 into a twisted pair configuration minimizes the noise generated due to the loop area enclosed by the lead wires, but, does not address the noise due to triboelectric effects.

Previous attempts to minimize the noise due to the lead wires 10 and 15 connected between the EEG probes 20 and 25 and the amplifier 40, at best, addressed only one or two of the sources of noise; and, thus, are not satisfactory for reducing the noise due to the lead wires connected between EEG probes and associated amplifier.

SUMMARY OF THE INVENTION

It is an object of the present invention to provide a low noise EEG probe wiring system.

It is another object of the present invention to provide a low noise EEG probe wiring system capable of minimizing the noise due to the lead wires connected between EEG probes and an associated amplifier.

It is still another object of the present invention to provide a low noise EEG probe wiring system capable of minimizing the noise due to the loop enclosed by the lead wires connected between EEG probes and an associated amplifer, electrostatic noise potentially picked up by the lead wires, microphonic noise, and noise due to triboelectric effects.

It is a further object of the present invention to provide a low noise EEG probe wiring sytem suitable or use in an evoked potential autorefractometry system.

To achieve the above objects of the present invention, the present invention includes a pair of coaxial cables. The coaxial cables are positioned in contact with each other along the length of the cables with a third braid shield positioned around the pair of coaxial cables when they are in contact and and around the cables when they are not in contact. A second insulator layer is positioned around the second braid shield.

The combination of coaxial cables being double shielded along their entire length, and preferably having graphite coated insulating layers and being positioned in contact with each other results in a low noise EEG probe wiring system that minimizes the noise due to (1) the area enclosed by the pair of coaxial cables, (2) electrostatic noise potentially picked up by the coaxial cables, and (3) microphonic effects such as variable capacitance between the cables and bending and vibration of the cables, and (4) triboelectric effects such as bending.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 2:
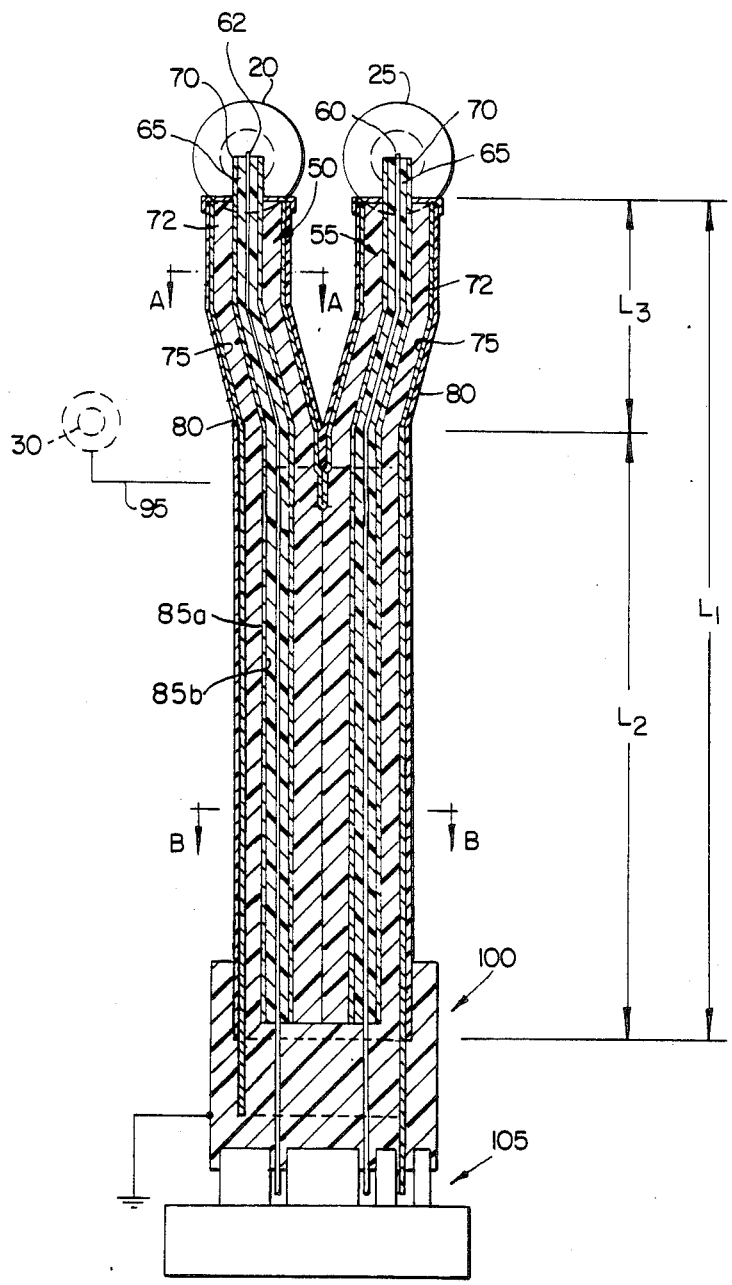
FIG. 2 illustrates a cross-section of the low noise EEG probe wiring system according to the present invention.

Referring to FIG. 2, a preferred embodiment of the present invention includes a pair of coaxial cables 50 and 55 of length L1 include central conductors 62 and 60, a graphite coated insulating layer 65, a first braid shield 70, a second insulator layer 72, a second or external braid shield 75 and a third insulator layer 80. As shown in FIG. 2, the pair of coaxial cables 50 and 55 are positioned in contact with each other for the entire length L2.

To enable the EEG probes to be positioned on various areas of a subject's head a length of the EEG probe wiring system, L3, comprises the two coaxial cables 50 and 55 separated from each other. Minimizing the length L3 is necessary to minimize the loop noise pick up area defined by the separate coaxial cables 50 and 55. The length L3 should be long enough to reach the area of the head to which an EEG is to be attached, for example, in the range of not more than 4–6 inches.

Figure 3:
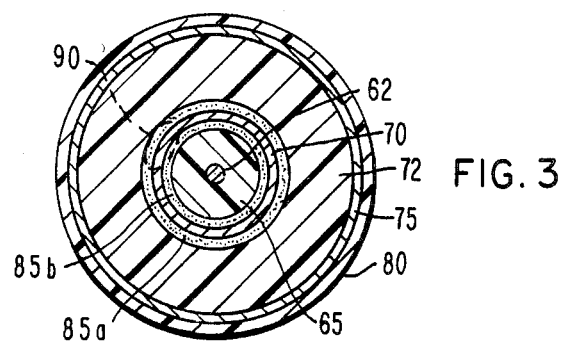
FIG. 3 is a cross-sectional view of one of the coaxial cables shown in FIG. 2 along the line A—A.

FIG. 3 illustrates a cross-sectional view along the line A—A of the coaxial cable 50 shown in FIG. 2. In a preferred embodiment of the present invention, the coaxial cables 50 and 55 comprise "Micro Dot" coaxial cables part number LN-1 manufactured by Mirotech, 1420 Conchester Hwy., Boothwyn Pa. As shown in FIG. 3 such a "Micro Dot" cable includes a central conductor 60, 62 and a graphite coated polyethelene insulating layer 65 formed around and intimately bonded to the central conductor 60, 62. The outer surface of the insulating layer 65 facing the braid 70 is coated with graphite and an additional coating can be applied to the outside of shield 70. Graphite coatings are schematically represented by the areas denoted by reference numeral 85a and 85b. The graphite layers 85a and 85b eliminates the noise due to triboelectric effects, and substantially eliminates friction between the insulating layer 65 and the braid shield 70. For example, if the cable is bent, then the insulating layer 65 and braid shield 70 rub against each other in the region 90. This rubbing causes a charge to build up which capacitively couples to the central conductor 60, 62 causing noise in the signal sought to be measured. Such a charge build up is substantially eliminated by coating the insulating layer 65 with graphite. Rubbing between the central conductor 60, 62 and the insulating layer 65, does not occur because the insulator is bonded to the center conductor rubbing between the insulating layer 65 and the braid shield 70 occurs not only when the cable is bent but, when the cable is vibrated due to, for example, machinery operating in a room next to the cable, or by people walking across the floor on which a cable is resting. The noise generated by such triboelectric effects significantly degrades the effectiveness of an EEG measuring system to the point where expensive signal processing equipment such as a high quality low pass filter must be employed to detect the EEG signals sought to be measured. The graphite coated insulating layer 65 minimizes and substantially eliminates these effects. The outside layer of the "Micro Dot" coaxial cable is the teflon jacket 72.

Figure 1:
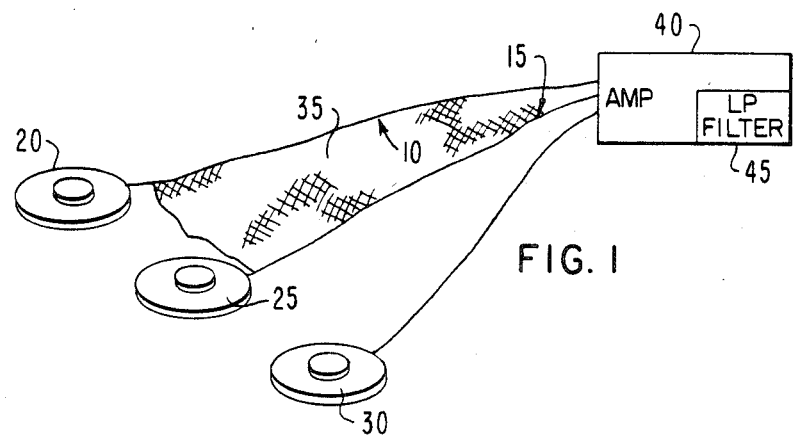
FIG. 1 schematically illustrates a conventional EEG probe wiring system.

As shown in FIG. 2, the EEG wiring system of the present invention is double shielded by the coaxial braid shield 70 and the external braid shield 75. These braid shields function to shield the central conductors 60 and 62 from electrostatic noise throughout the entire length, L1, of the EEG probe wiring system from an amplifier 40 (FIG. 1) to the probes 20 and 25.

A reference lead 95, shown in FIG. 2, is soldered to the external braid shield 75 and attached to the EEG probe 30. The EEG probe 30 is attached to, for example, the ear of a subject and provides a reference potential for measuring a differential voltage between the EEG probes 20 and 25. As an alternative, the reference lead could comprise a coaxial cable positioned wihtin the braid shield 75.

In the preferred embodiment, insulator layer 80 comprises heat shrink tubing. As is conventional practice, before being shrunk, the heat shrink tubing is of a larger diameter than the coaxial cables 50, 55 and external braid shield 75 placed therein. After placing the coaxial cables and braid shield within the heat shrink tubing, a hand held dryer can be used to heat the tubing, causing it to shrink and mold itself around the braid shield 75 housing coaxial cables 50 and 55. The insulator layer 80 protects the braid shield 75 from coming contact with, for example, a high voltage such as 110 volts which can commonly be exposed in a laboratory. The heat shrink tubing 80 also functions to hold the coaxial cables 50 and 55 in contact with each other throughout the entire length L3, as shown in FIG. 2.

In FIG. 2, reference numeral 100 illustrates a cut away view of an outer metal jacket for a gold contact metal plug used to connect the coaxial cables 50 and 55 to the amplifier 40. As illustrated, both the braid shield 70 is connected to the gold reference contact of the metal jacket plug 100 and and then to the signal reference ground at the amplifier 40. The braid shield terminates within the metal jacket plug but is not electrically connected at the plug end. The metal jacket connects to the amplifier chassis outer use of the gold contact metal jacketed plug eliminates electrostatic noise due to friction between the plug and the amplifier connector 105.

Figure 4:
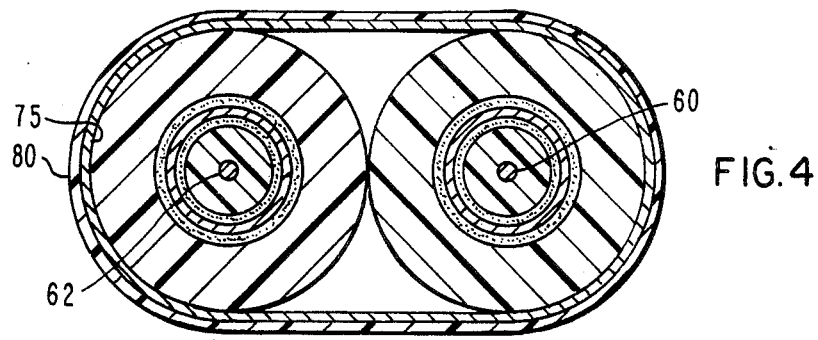
FIG. 4 is a cross-sectional view of the pair of coaxial cables shown in FIG. 2 along the line B—B.

FIG. 4 is a cross-sectional view along the line B—B of the EEG probe wiring system shown in FIG. 2. As seen in FIG. 4, the composite cable has an oval shape. This shape results from the coaxial cables being placed adjacent to each other. Other shapes are possible depending upon, for example, whether or not the cables are formed in a twisted pair configuration or whether more than two coaxial cables are provided inside braid 75.

Because the EEG probe wiring system of the present invention insures that the coaxial cables 50 and 55 are held in contact with one another throughout the length L3 (FIG. 2) the noise due to the loop area enclosed by the cables is practically eliminated. Furthermore, double shielding the coaxial cables via braid shields 70 and 75 throughout the entire length of the cables from the amplifier 40 to the EEG probes 20 and 25 with no openings in the shield together with the braid shields 70 and 75 being electrically connected at the probes 20 and 25 and by means of the inner shield 70 connected to the gold reference contact of the metal jacketed plug 100 at the amplifier 40 significantly minimizes any electrostatic noise that may enter the measuring system through the EEG probe wiring.

The graphite coated insulating layer 65 substantially eliminates noise due to triboelectric effects created by bending the cable or due to cable vibrations induced by, for example, persons walking across the floor on which the cable is positioned, or by vibrations of a machine operating in a nearby room.

The cables 50 and 55 can also be twisted in a twisted pair configuration within the braid shield 75 and heat shrink tubing 80 throughout the length L3. Such twisting provides further electrostatic and magnetic shielding. Such a configuration, however, is more difficult to place within the braid shield 75 and heat shrink tubing 80.

The combination of housing coaxial cables in contact with one another from an amplifier to a point just short of EEG probes, double shielding the coaxial cables from an amplifier to EEG probes and employing graphite coated insulation within the coaxial cables results in a low noise EEG probe wiring system substantially eliminating noise due to the loop that the cables enclose, electrostatic noise, microphonic and noise due to triboelectric effects.

The many features and advantages of the invention are apparent from the detailed specification and thus it is intended by the appended claims to cover all such features and advantages of the system which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A low noise electroencephalographic (EEG) probe wiring system for connection between an amplifier and at least a pair of EEG probes, comprising:
   a pair of coaxial cables each having a length and including:
   a central conductor having one end for connection to one pair of EEG probes and a second end for connection to an amplifier;
   a graphite coated polyethylene layer positioned around and bonded to the central conductor;
   a first conductive braid shield positioned about the graphite coated layer along said length, having a first end and a second end;
   a PTFE jacket positioned around said first conductive braid shield along said length; and
   said coaxial cables being positioned in contact with each other along a substantially parallel path and along a first portion of said length of said coaxial cables;
   a second conductive braid shield having a first braid portion positioned around said pair of coaxial cables and along said first portion of said length, and a second braid portion positioned around respective ones of said coaxial cables along the remaining portion of said length of said cables, said second conductive braid shield having a first end connected to said first end of said first conductive braid shield, a second end and a junction between said first and second braid portions of said second conductive braid shield;
   heat shrink tubing positioned around said second conductive braid shield;
   a reference lead, connected to said second conductive braid shield at said junction, for connection to an additional reference EEG probe; and
   gold contact metal jacket means for connecting the second end of each of said coaxial cables and the second end of said second conductive braid shield to the amplifier, a portion of the jacket means being connected to a ground potential.

2. A low noise EEG probe wiring system according to claim 1, wherein said length is within the range of 2–25 feet and said remaining portion of said length is in the range of 4–6 inches.

* * * * *